United States Patent
Aho et al.

(10) Patent No.: US 6,201,027 B1
(45) Date of Patent: Mar. 13, 2001

(54) SUBSTITUTED β DIKETONES AND THEIR USE

(75) Inventors: Päivi Aho; Reijo Bäckström, both of Helsinki; Anita Koponen; Inge-Britt Linden, both of Espoo; Timo Lotta, Vantaa; Kari Lönnberg, Routio; Aino Pippuri, Espoo; Pentti Pohto, Helsinki, all of (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/346,397

(22) Filed: Jul. 1, 1999

(51) Int. Cl.[7] .......................... A61K 31/10; C07C 317/14

(52) U.S. Cl. .......................... 514/710; 514/675; 514/709; 568/28; 568/31

(58) Field of Search .................... 568/28, 31; 514/675, 514/709, 710

(56) References Cited

U.S. PATENT DOCUMENTS

| | | | |
|---|---|---|---|
| 4,741,769 | 5/1988 | Lee | 71/123 |
| 5,292,771 | * 3/1994 | Backstrom et al. | 514/472 |
| 5,804,532 | * 9/1998 | Cain et al. | 504/309 |

FOREIGN PATENT DOCUMENTS

| | | |
|---|---|---|
| 37 40 383 A1 | 6/1988 | (DE) . |
| 0 323 162 A2 | 7/1989 | (EP) . |
| 0 440 324 A2 | 8/1991 | (EP) . |
| 0 357 403 B1 | 12/1994 | (EP) . |
| 62-30767 | 2/1987 | (JP) . |

OTHER PUBLICATIONS

CA:130:234068 abs of WO9915168, Apr. 1999.*
CA:128:289576 ags of Drugs Future by Wrobleski et al, 23(1) pp. 28–31, 1998.*
Aho, P. et al., abstract of presentation entitled "Protection in Rat Colitis Models by the Sulfhydryl Modulating Compound OR–1364," Falk Symposium No. 67, "Inflammatory Bowel Diseases—Pathophysiology as Basis of Treatment", in Regensburg, Germany, Jun. 25–27, 1992.
Aho, P. et al., poster presentation entitled "Protection in Rat Colitis Models by the Sulfhydryl Modulating Compound OR–1364," Falk Symposium No. 67, "Inflammatory Bowel Diseases—Pathophysiology as Basis of Treatment", in Regensburg, Germany, Jun. 25–27, 1992.
Aho, P. et al., abstract of presentation entitled "The Sulfhydryl Modulating Compound OR–1364 Protects Against Free Radical Induced Colitis in Rats," American Gastroenterological Association Conference in Boston, MA, May 15–19, 1993.
Aho, P. et al., poster presentation entitled "The Sulfhydryl Modulating Compound OR–1364 Protects Against Free Radical Induced Colitis in Rats," American Gastroenterological Association Conference in Boston, MA, May 15–19, 1993.
Aho, P. et al., abstract of presentation entitled "Protection in Rat Colitis Models by the Sulfhydryl Modulating Compound OR–1364," 26th Nordic Meeting of Gastroenterology in Tampere, Finland, May 26–29, 1993.
Aho, P. et al., abstract of presentation entitled "OR–1364 inhibits the Development of Immune Complex Colitis in Rabbits," American Gastroenterology Association Digestive Disease Week in New Orleans, LA, May 15–18, 1994.
Aho, P. et al., poster presentation entitled "OR–1364 Inhibits the Development of Immune Complex Colitis in Rabbits," American Gastroenterology Association Digestive Disease Week in New Orleans, LA, May 15–18, 1994.
Aho, P., et al., abstract of presentation entitled "Protection Against Immune Complex–Induced Colitis in Rabbits by OR–1364," 3rd United European Gastroenterology Week in Oslo, Norway, Jun. 25–29, 1994.
Aho, P., et al., poster presentation entitled "Protection Against Immune Complex–Induced Colitis in Rabbits by OR–1364," 3rd United European Gastroenterology Week in Oslo, Norway, Jun. 25–29, 1994.
Aho, P. et al., abstract of presentation entitled "OR–1364, A Novel Locally Acting Compound for the Treatment of Inflammatory Bowel Diseases," Falk Symposium No. 85, "Inflammatory Bowel Diseases," in Den Haag, The Netherlands, Jun. 29–Jul. 1, 1995.
Aho, P. et al., "Hapten–Induced Murine Colitis—A Useful Model For Studying Tissue Levels of Cytokines," *Gastroenterology* 110:A852 (1996).
Aho, P. et al., abstract of presentation entitled "OR–1384, A Novel Locally Acting Immunomodulating Agent, Protects Against Experimental Colitis," Annual Meetings of the American Gastroenterological Association, American Association for the Study of Liver Diseases, May 11–14, 1997.

(List continued on next page.)

Primary Examiner—Jean F Vollano
(74) Attorney, Agent, or Firm—Sterne, Kessler, Goldstein & Fox, P.L.L.C.

(57) ABSTRACT

The invention relates to the compounds of formula I:

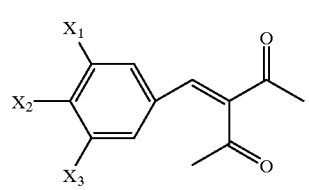

wherein one of $X_1$ and $X_2$ is $MeSO_2$ and the other one is hydrogen or halogen and $X_3$ is hydrogen or halogen. These compounds have been found to be useful in the prevention and the treatment of respiratory diseases, especially asthma, ARDS (Acute Respiratory Distress Syndrome), COPD (chronic obstructive pulmonary diseases), allergic rhinitis and related inflammatory conditions. More specifically, the invention relates to the use of said compound in the prevention and the treatment of asthma in steroid-resistant patients. The invention also relates to pharmaceutical formulations used in the treatment of said diseases.

17 Claims, 2 Drawing Sheets

OTHER PUBLICATIONS

Heinonen, T. et al., abstract of presentation entitled "Simulation of In Vivo Conditions in Cell Culture by Coculturing Techniques," The 15$^{th}$ Anniversary Meeting of the Finnish Society of Toxicology in Kuopio, Finland, Apr. 22–23, 1994.

Heinonen, T. et al., poster presentation entitled "Simulation of In Vivo Conditions in Cell Culture: Epithelial Cell Monolayers Cultured on Permeable Support," The 15$^{th}$ Anniversary Meeting of the Finnish Society of Toxicology in Kuopio, Finland, Apr. 22–23, 1994.

Koponen, A. et al., abstract of presentation entitled "Protection Against Immune Complex–Induced Colitis in Rabbits by OR–1364," Falk Symposium No. 76, "Inflammatory Bowel Diseases: New Insights into Mechanisms of Inflammation and Challenges in Diagnosis and Treatment," in Cascais, Portugal, May 5–7, 1994.

Koponen, A. et al., poster presentation entitled "Protection Against Immune Complex–Induced Colitis in Rabbits by OR–1364," Falk Symposium No. 76, "Inflammatory Bowel Diseases: New Insights into Mechanisms of Inflammation and Challenges in Diagnosis and Treatment," in Cascais, Portugal, May 5–7, 1994.

Laulajainen, T. et al., abstract of presentation entitled "Inhibition of Cytokine Release From Mononuclear Cells by OR–1364," Falk Symposium No. 76, "Inflammatory Bowel Diseases: New Insights into Mechanisms of Inflammation and Challenges in Diagnosis and Treatment," in Cascais, Portugal, May 5–7, 1994.

Laulajainen, T. et al., poster presentation entitled "Inhibition of Cytokine Release From Mononuclear Cells by OR–1364," Falk Symposium No. 76, "Inflammatory Bowel Diseases: New Insights into Mechanisms of Inflammation and Challenges in Diagnosis and Treatment," in Cascais, Portugal, May 5–7, 1994.

Laulajainen, T. et al., abstract of presentation entitled "Effect of OR–1364 on Cytokine Release in Epithelial–Mononuclear Cell Co–Cultures," Meetings of the American Gastroenterological Association, American Association for the Study of Liver Diseases at Digestive Disease Week, in San Diego, CA, May 10–13, 1992.

Lindén, I.–B. et al., abstract of presentation entitled "Protection in Acute and Chronic Colitis Models by the Sulfhydryl Modulating Compound OR–1364," American Gastroenterological Association Conference in San Francisco, CA, May 10–13, 1992.

Lindén, I.–B. et al., poster presentation entitled, "Protection in Acute and Chronic Colitis Models by the Sulfhydryl Modulating Compound OR–1364," AGA Conference in San Francisco, CA, May 10–13, 1992.

NIH Publication No. 97–4051, "Guidelines for the Diagnosis and Management of Asthma," National Institutes of Health, National Heart, Lung and Blood Institute, Jul. 1997.

Nissinen, E. et al., "Inhibition of Neutrophil Activation by a Novel Thiolmodulating Compound OR–1384," *Archives Pharmacol.* 358:R668, abstract P 23.18 (Jul. 1998).

Nissinen, E. et al., abstract of presentation entitled "Suppression of Neutrophil–Derived Inflammatory Mediator Production by OR–1364," 4$^{th}$ International Symposium on Inflammatory Bowel Diseases in Strasbourg, France, Sep. 6–8, 1993.

Nissinen, E. et al., abstract of presentation entitled "Suppression of Neutrophil and T–Lymphocyte Activation by an Anticolitis Agent OR–1364," American Gastroenterology Association Digestive Disease Week in New Orleans, LA, May 15–18, 1994.

Nissinen, E. et al., poster presentation entitled "Suppression of Neutrophil–Derived Oxygen Radical Production by the Reversible Thiol Reagent OR–1364," 3$^{rd}$ United European Gastroenterology week in Oslo, Norway, Jun. 25–29, 1994.

Nissinen, E. et al., abstract of presentation entitled "Suppression of Cytokine Production and Neutrophil Activation by an Immunomodulating Agent OR–1384," Annual Meetings of the American Gastroenterological Association, American Association for the Study of Liver Diseases, May 11–14, 1997.

Penttilä, K.E. et al., abstract of presentation entitled "Transient Activation of Microsomal Glutathione S–Transferase In Vitro as an Indicator of Reversible Binding of OR–1364 to Protein Thiols," The 15$^{th}$ Anniversary Meeting of the Finnish Society of Toxicology in Kuopio, Finland, Apr. 22–23, 1994.

Penttilä, K.E. et al., poster presentation entitled "Transient Activation of Microsomal Glutathione S–Transferase In Vitro as an Indicator of Reversible Binding of OR–1364 to Protein Thiols," The 15$^{th}$ Anniversary Meeting of the Finnish Society of Toxicology in Kuopio, Finland, Apr. 22–23, 1994.

Penttilä, K.E. et al., "Suppression of IL–1β and IL–2 Production in THP–1 Monocytic Cells and Jurkat T Cells by Immunomodulating Agent OR–1384," FEBS Special Meeting '97 in Amsterdam, The Netherlands, Jun. 29–Jul. 3, 1997.

Serkkola, E. et al., "Inhibition of LPS–Induced Cytokine Production in Mononuclear Cells by Orazipone (OR–1384)," 9$^{th}$ International Conference of Inflammation Research Association, Hershey, PA, Nov. 1–5, 1998.

Serkkola, E. and E. Nissinen, "The Effect of Orazipone on LPS–Induced IL–1β and TNFα Production," *Mediators of Inflammation* 8:S84 (1999).

Whelan, C.J., "Inhibition of PAF–, LPS–, and cytokine–induced granulocyte accumulation in guinea pig lung by dexamethasone: Evidence that inhibition of IL–5 release is responsible for the selective inhibition of eosinophilia by glucocorticoids in guinea–pigs," *Inflamm. Res.* 45:166–170 (1996).

Whelan, C.J. et al., "Inhibition of some aspects of acute inflammation of guinea–pig lung by intraperitoneal dexamethasone and mifepristone: Demonstration of agonist activity of mifepristone in the guinea–pig," *Inflamm. Res.* 44:131–138 (1995).

English language abstract of Document No. AL1, Japanese Patent No. 62–30767 A, Derwent World Patents Index, WPI Accession No. 87–076907/198711.

English language abstract of Document No. AM1, German Patent No. 37 40 383 A1, Derwent World Patents Index, WPI Accession No. 88–156069/198823.

* cited by examiner

SUBSTITUTED β DIKETONES AND THEIR USE

FIELD OF THE INVENTION

The invention relates to new and known substituted β-diketones, more precisely, phenyl-methylene-2,4-pentanedione derivatives, to their preparation and use in the prevention and the treatment of respiratory diseases, especially asthma, ARDS (Acute Respiratory Distress Syndrome), COPD (chronic obstructive pulmonary diseases), allergic rhinitis and related inflammatory conditions. More specifically, the invention relates to the use of said compounds in the prevention and the treatment of asthma in steroid-resistant patients. The invention also relates to pharmaceutical formulations used in the treatment of said diseases.

BACKGROUND OF THE INVENTION

Asthma is a chronic inflammatory disease of the airways characterized by eosinophil accumulation into the lung and hyperreactivity of the airways. The disease has a wide spectrum from mild symptoms to deaths. Atopic asthma is an allergic disease where the airways-hyperreactivity is the most typical feature and occurs most often in children. When the disease occurs in older people it is very often so called intrinsic asthma. Characteristic for this subtype of asthma is a more prominent inflammation of the airways than in atopic asthma.

The most effective drugs for asthma today are inhaled corticosteroids. All currently available inhaled steroids are absorbed systemically from the lungs. The most important adverse effect of long term treatment with corticosteroids is the suppression of endogenous cortisol production by adrenals. An ideal drug for asthma would have a powerful anti-inflammatory effect locally at the airways but no systemic effects. A subset of patients with asthma are steroid-resistant. For these patients there is a need for a new drug, which does not act through the same mechanism as corticosteroids but has the same inhibitory effect on the inflammatory cells. Today methotrexate, cyclosporin and immunoglobulin are used for treatment of steroid resistant asthma. These drugs are systemically acting and thus cause serious adverse effects.

EP-A-0 440 324 discloses substituted β-diketones which are suggested to be useful in the treatment of inflammatory bowel disease (IBD). The compounds of EP-A-0 440 324 were tested using the so called TNB-induced chronic colitis model in rats. The most promising compound OR 1364 (3-[(3-cyanophenyl)methylene]-2,4-pentanedione) has been extensively studied in the treatment of IBD and taken to clinical trials. Unfortunately, the trials had to be discontinued because the compound was found to be irritating.

SUMMARY OF THE INVENTION

The invention is directed to a new type of locally acting, nontoxic, medicament for the prevention and treatment of respiratory diseases, especially asthma. The compounds of the invention are new, except for 3-[(4-methylsulfonylphenyl)methylene]-2,4-pentanedione), the use of which in the treatment of inflammatory bowel disease has been disclosed earlier in EP-A-0440324.

Accordingly, the invention provides a compound of general formula I:

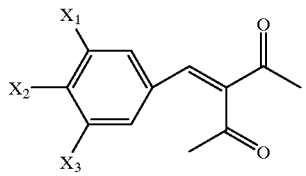

wherein one of $X_1$ and $X_2$ is $MeSO_2$ and the other one is halogen and $X_3$ is hydrogen or halogen.

The invention further provides a method for the use of compounds of general formula I' to prevent or treat respiratory diseases:

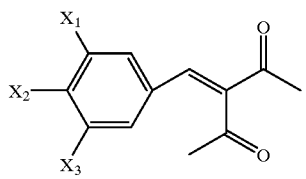

wherein, in formula I', one of $X_1$ and $X_2$ is $MeSO_2$ and the other one is hydrogen or halogen and $X_3$ is hydrogen or halogen. Most preferable in this indication are the compounds of formula I (I') wherein $X_1$ is halogen, $X_2$ is $MeSO_2$ and $X_3$ is hydrogen. Especially preferably $X_1$ is chloro.

The invention further provides a method for the manufacture of a medicament for use in the treatment of respiratory diseases.

The invention also provides new, valuable intermediates having formula II':

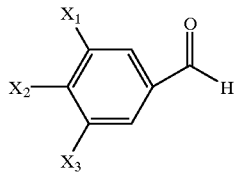

wherein one of $X_1$ and $X_2$ is $MeSO_2$ and the other one bromo or fluoro and $X_3$ is hydrogen or halogen, and methods for their use.

DETAILED DESCRIPTION OF THE PREFERRED EMBODIMENTS

Figure 1:
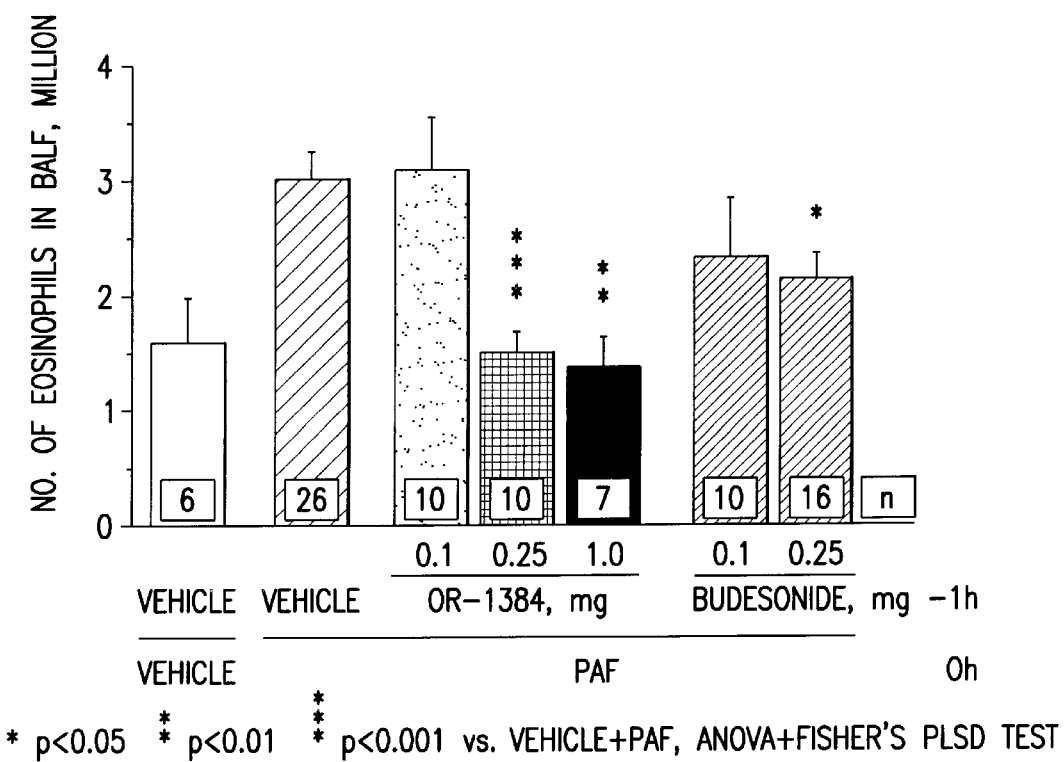
FIG. 1 shows the effect of 3-[(4-methylsulfonylphenyl)methylene]-2,4-pentanedione (test compound OR 1384) and the reference compound, budesonide on PAF-induced eosinophil accumulation.

The compounds of invention which are new have the following general formula I:

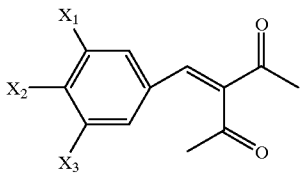

I wherein one of $X_1$ and $X_2$ is $MeSO_2$ and the other one is halogen and $X_3$ is hydrogen or halogen.

As used herein, the term halogen means here a chloro, bromo or fluoro substituent.

The invention further provides a method for the use of compounds of general formula I':

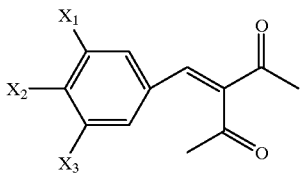

I' wherein one of $X_1$ and $X_2$ is $MeSO_2$ and the other one is hydrogen or halogen and $X_3$ is hydrogen or halogen. Compounds of the formula I and I' are useful to prevent or treat respiratory diseases, especially asthma, ARDS (Acute Respiratory Distress Syndrome), COPD (chronic obstructive pulmonary diseases), allergic rhinitis and related inflammatory conditions, and most preferably, asthma in steroid-resistant patients. Most preferable in these indications are the compounds of formula I (and I') wherein $X_1$ is halogen, $X_2$ is $MeSO_2$ and $X_3$ is hydrogen. Especially preferably $X_1$ is chloro.

It has now been found out that compounds of the invention work in the same way as budesonide, a conventional anti-asthma corticosteroid. Because the compounds of the invention act locally and decompose in the blood circulation, they are excellent candidates for the treatment of asthma, especially in those patients who cannot use traditional steroid therapy. Furthermore, the compounds of the invention do not have the harmful irritative properties of OR 1364.

The compounds of the invention have potential independently of whether the condition to be treated has its origin in intrinsic or atopic type of asthma. In addition to the treatment of human patients, the compounds of the invention are also useful in veterinary medicine, for the treatment of non-human animal patients.

The compounds of the invention may be prepared by the same principles as described in EP-A-0 440 324, incorporated herein by reference. Accordingly, the compound of formula II:

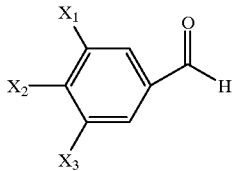

II (wherein $X_1$ to $X_3$ are the same as defined above for formula I) is allowed to react in the presence of an acidic or basic catalyst with a compound of formula III having an active methylene group

$$CH_3-CO-CH_2-CO-CH_3$$

III to produce the compound of formula I.

Especially useful are new, valuable intermediates having formula II':

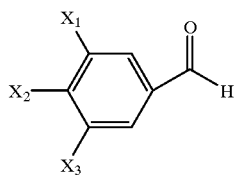

II' wherein one of $X_1$ and $X_2$ is $MeSO_2$ and the other one bromo or fluoro and $X_3$ is hydrogen or halogen.

When delivered to the airways, to ascertain that the medicament containing efficacious amounts of the desired compound of the invention reaches its location of action in the airways, it is preferable to reduce the particle size of the active ingredient powder, e.g. by micronization. Accordingly, the invention further provides an inhalable pharmaceutical formulation containing a compound according to formula I, having preferably about 100% of its particle size below 10 μm, more preferably about 95% being below 5.0 μm, optionally in a suitable carrier or diluent. The amount of the active ingredient is preferably about 0.1 to 100% (w/w), more preferably about 1–50% based on the total weight of the formulation.

The effective dose of the compound varies depending on the individual, severity and stage of the disease. The effective dose for the adult human, especially a male, will range from about 500 μg to about 5 mg per day, preferably 1–2 mg per day. Animal dosages are proportionately less, based upon body weight.

The compounds according to this invention may be given to a patient as such or in combination with one or more other active ingredients and/or suitable pharmaceutically advantageous additives and/or excipients. These groups comprise primarily a carrier suitable for compositions which are intended for pulmonary delivery, optionally with the addition of solubilizers, buffering, stabilizing, flavoring, colonizing and/or preserving agents.

Examples of suitable solid carriers are saccharide particles, e.g. lactose having larger particle size than the active substance, preferably 5–100 μm. Aerosol carriers, especially non-chlorofluorocarbon-based carriers, may also be used, e.g. HFA (hydrofluoroalkane) based aerosols. The use of aqueous carriers is also possible. However, dry inhalation formulations are preferred.

The formulations may be administered using conventional delivery techniques. Dry inhalation powders may be packed, e.g. in hard gelatine capsule s or a blister package to be given in single units or directly in dry powder inhalers, e.g. multi-dose devices. Aerosols may be given from pressurized metered dose inhalers (PMDI) and aqueous suspensions from nebulizers.

EXAMPLES

Example 1

3-{[3-Fluoro-4-(methylsulfonyl)-phenyl]
methylene}-2,4-pentanedione
3-Fluoro-4-methylsulfonylbenzaldehyde To a solution containing 0.5 g 3,4-difluorobenzaldehyde and 20 ml DMSO was added 0.71 g methanesulfinic acid sodium salt with stirring at 90° C. The solution was stirred 6 hours at 90° C. and then poured into water. Sodiumhydrogencarbonate was added and the product was extracted with ethyl acetate. The extract was evaporated to dryness in vacuo. The residue was triturated with 2-propanol, yield 0.93 g. $^1$H-NMR (DMSO-$d_6$, 400 MHz): 3.52 (s, 3 H, $CH_3$), 7.98–8.13 (m, 3 H, Ar), 10.22 (d, 1 H, CHO).

3-{[3-Fluoro-4-(methylsulfonyl)-phenyl]methylene}-2,4-pentanedione

To a solution containing 0.93 g 3-fluoro-4-methylsulfonylbenzaldehyde, 0.05 ml piperidine and 0.02 ml formic acid in 20 ml DMF was added 1.04 ml 2,4-pentanedione with stirring at 20° C. The solution was stirred overnight at 20° C. and poured into water. The product was extracted with ethyl acetate and washed with water and evaporated to dryness in vacuo. The residue was crystallized from methanol, yield 0.48 g (30%), mp. 140–143° C. $^1$H-NMR (DMSO-$d_6$, 400 MHz): 2.28 (s, 3 H, $CH_3$), 2.50 (s, 3 H, $CH_3$), 3.36 (s, 3 H, $CH_3$), 7.47 (m, 1 H, Ar), 7.93 (m, 2 H, Ar), 7.76 (s, 1 H, CH).

Example 2

3-{[3-Chloro-4-methylsulfonyl)-phenyl]methylene}-2,4-pentanedione

3-Chloro-4-methylsulfonylbenzaldehyde

To a solution containing 1.0 g 4-fluoro-3-chlorobenzaldehyde and 45 ml DMSO, was added 1.93 g methanesulfinic acid sodium salt with stirring at 90° C. The solution was stirred 6 hours at 90° C. and poured into water. Sodiumhydrogencarbonate was added and the product was extracted with ethyl acetate. The extract was evaporated to dryness in vacuo. The residue was triturated with 2-propanol, yield 1.06 g. $^1$H-NMR (DMSO-$d_6$, 400 MHz): 3.45 (s, 3H, $CH_3$), 8.09–8.27 (m, 3 H, Ar), 10.01 (d, 1 H, CHO).

3-{[3-Chloro-4-(methylsulfonyl)-phenyl]methylene}-2,4-pentanedione

To a solution containing 1.42 g 3-chloro-4-methylsulfonylbenzaldehyde, 0.05 ml piperidine and 0.02 ml formic acid in 20 ml DMF was added 1.50 ml 2,4-pentanedione with stirring at 20° C. The solution was stirred overnight at 20° C. and poured into water. The oily residue was separated and crystallized from ethanol, yield 0.24 g (10%), mp. 140–142° C. $^1$H-NMR (DMSO-$d_6$, 400 MHz): 2.28 (s, 3 H, $CH_3$), 2.50 (s, 3 H, $CH_3$), 3.40 (s, 3 H, $CH_3$), 7.60 (m, 1 H, Ar), 7.80 (m, 1 H, Ar), 7.77 (s, 1 H, CH), 8.1 (m, 1 H, Ar).

Example 3

3-{[3-Bromo-4-(methylsulfonyl)-phenyl]methylene}-2,4-pentanedione

3-Bromo-4-methylsulfonylbenzaldehyde

To a solution containing 0.5 g 3-bromo-4-fluorobenzaldehyde and 20 ml of DMSO was added 0.49 g methanesulfinic acid sodium salt with stirring at 90° C. The solution was stirred 6 hours at 90° C. and poured into water. Sodiumhydrogencarbonate was added and the product extract with ethyl acetate. The extract was evaporated to dryness in vacuo. The residue was triturated with 2-propanol, yield 0.69 g. $^1$H-NMR (DMSO-$d_6$, 400 MHz): 3.52 (s, 3 H, $CH_3$), 8.10–8.47 (m, 3 H, Ar), 10.01 (d, 1 H, CHO).

3-{[3-Bromo-4-(methylsulfonyl)-phenyl]methylene}-2,4-pentanedione

To a solution containing 0.68 g 3-bromo-4-methylsulfonylbenzaldehyde, 0.03 ml piperidine and 0.02 ml formic acid in 20 ml DMF was added 0.59 ml 2,4-pentanedione with stirring at 20° C. The solution was stirred overnight at 20° C. and poured into water. The product was extracted with ethyl acetate, washed with water and evaporated to dryness in vacuo. The residue was crystallized from methanol, yield 0.18 g (20%), mp 135–139° C. $^1$H-NMR (DMSO-$d_6$, 400 MHz): 2.28 (s, 3 H, $CH_3$), 2.50 (s, 3 H, $CH_3$), 3.36 (s, 3 H, $CH_3$), 7.60 (d, 1 H, Ar), 7.99 (d, 1 H, Ar), 8.12 (d, 1 H, Ar), 7.71 (s, 1 H, CH).

Example 4

3-{[3,5-Dichloro-4-(methylsulfonyl)phenyl]methylene}-2,4-pentanedione 3,5-Dichloro-4-[(carboxymethyl)thio]benzoic acid ethyl ester 4-Amino-3,5-dichlorobenzoic acid ethyl ester (17.7 g) was dissolved in a mixture of acetic acid (75 mL) and dichloromethane (75 mL) and then methanesulfonic acid (22 mL) was added. 3-Methylbutyl nitrite (10 mL) was added to the solution while the temperature was kept at 0–5° C. After 30 min, mercaptoacetic acid (38 mL) was added at 0–5° C. Then a part of the dichloromethane was removed by distillation which was stopped when the internal temperature of the mixture was 80° C. and this temperature was kept for additional 45 min. The mixture was cooled and the rest of the solvents were evaporated under vacuum. Toluene (300 mL), water (200 mL) and hydrochloric acid (6 M, 80 mL) were added. The organic phase was separated and then extracted with potassium bicarbonate solution (1 M, 200 mL) which was acidified with hydrochloric acid (6M, 50 mL). The product was extracted to toluene (100 mL) which was dried (sodium sulphate) and evaporated to dryness (yield 5.1 g). $^1$H-NMR (400 MHz, DMSO-$d_6$) d=1.33 (t, J=7.0 Hz, 3H), 3.74 (s, 2H), 4.34 (q, J=7.0 Hz, 2H), 7.97 (s, 2H), 12.5 (b, 1H).

3,5-Dichloro-4-[(carboxymethyl)sulfonyl]benzoic acid ethyl ester 3,5-Dichloro-4-[(carboxymethyl)thio]benzoic acid ethyl ester (5.1 g) was dissolved in potassium bicarbonate solution (1 M, 50 mL). Then potassium permanganate solution (0.33 M in 0.42 M acetic acid, 150 mL) was slowly added at 20–30° C. (until the color of the permanganate was permanent). After 1 h stirring at 20–30° C., the residual permanganate was decolorized with saturated sodium pyrosulfite solution. The mixture was filtrated and the filtrate was acidified with hydrochloric acid (6 M) and the product was extracted with ethyl acetate. The extract was dried with sodium sulphate and evaporated to dryness (yield 3.1 g). $^1$H-NMR (400 MHz, DMSO-$d_6$) d=1.35 (t, J=7.0 Hz, 3H), 4.37 (q, J=7.0 Hz, 2H), 4.75 (s, 2H), 8.06 (s, 2H), 12.8 (b, 1H).

3,5-Dichloro-4-(methylsulfonyl)benzoic acid ethyl ester 3,5-Dichloro-4-[(carboxymethyl)sulfonyl]benzoic acid ethyl ester (3.1 g) was mixed with toluene (100 mL) and pyridine (1.0 mL) and the mixture was refluxed for 30 min and then evaporated to dryness (yield 2.6 g). $^1$H-NMR (400 MHz, DMSO-$d_6$) d=1.34 (t, J=7.0 Hz, 3H), 3.51 (s, 3H), 4.37 (q, J=7.0 Hz, 2H), 8.05 (s, 2H).

3,5-Dichloro-4-(methylsulfonyl)benzyl alcohol

To a solution of 3,5-dichloro-4-(methylsulfonyl)benzoic acid ethyl ester (2.6 g) in tetrahydrofuran (50 mL) was added lithium triethylborohydride (1 M in tetrahydrofuran, 24 mL) at 0–5° C. under nitrogen. The mixture was stirred for 30 min and then water (2 mL) was added and the tetrahydrofuran was evaporated under vacuum. Toluene (100 mL) and water (30 mL) were added and then hydrogen peroxide (30% in water, 20 mL) was added at 10–20° C. After 30 min, the separated solid was dissolved by adding ethyl acetate (100 mL). The organic phase was separated and washed with saturated sodium pyrosulfite solution (25 mL) and then with potassium bicarbonate solution (1 M, 25 mL) and then dried with sodium sulphate and evaporated to dryness (yield 1.8 g). $^1$H-NMR (400 MHz, DMSO-d$_6$) d=3.43 (s, 3H), 4.57 (s, 2H), 5.6 (b, 1H), 7.59 (s, 2H).

3,5-Dichloro-4-(methylsulfonyl)benzaldehyde 3,5-Dichloro-4-(methylsulfonyl)benzyl alcohol (1.7 g) was dissolved in dichloromethane (35 mL) and then active manganese(IV) oxide (7.0 g) was added and the mixture was stirred for 25 min at 22–28° C. The solid was removed by filtration and the filtrate was evaporated to dryness (yield 1.5 g). $^1$H-NMR (400 MHz, DMSO-d$_6$ d=3.53 (s, 3H), 8.12 (s, 2H), 10.02 (s, 1H).

3-{[3,5-Dichloro-4-(methylsulfonyl)phenyl]methylene}-2,4-pentanedione 3,5-Dichloro-4-(methylsulfonyl)benzaldehyde (1.5 g), 2-propanol (20 mL), 2,4-pentanedione (1.6 mL), formic acid (44 mL) and piperidine (114 mL) were mixed and stirred at 22–25° C. for 63 h. The product was filtered, washed with 2-propanol and dried (yield 1.0 g, melting point 134–136° C.). $^1$H-NMR(400 MHz, DMSO-d$_6$ d=2.29 (s, 3H), 2.46 (s, 3H), 3.48 (s, 3H), 7.67 (s, 2 H), 7.71 (s, 1H).

Example 5

3-{[4-Chloro-3-(methylsulfonyl)phenyl]methylene}-2,4-pentanedione

4-Chloro-3-[(carboxymethyl)sulfonyl]benzoic acid methyl ester

4-Chloro-3-aminobenzoic acid methyl ester (7.0 g) was suspended in a mixture of hydrochloric acid (1 M, 85 mL) and water (170 mL). A solution of sodium nitrite (2.59 g) in water (40 mL) was slowly added to the suspension at 0–5° C. temperature. After 40 min stirring at 0–5° C. solid urea (3.8 g) was added and dissolved by stirring. After 5 min a cold solution containing sodium acetate (12.7 g) and mercaptoacetic acid (13.0 mL) in water (85 mL) was added. Ethyl acetate (300 mL) was added and the solution was then refluxed for 60 min. The mixture was cooled and ethyl acetate (100 ml) and hydrochloric acid (6 M, 50 mL) were added. The organic phase was separated and the product extracted from it to potassium bicarbonate solution (1 M, 200 mL). The solution was acidified with 6 M hydrochloric acid and then extracted with ethyl acetate (200 mL). The ethyl acetate extract was dried with sodium sulphate and evaporated to dryness to give impure 4-chloro-3-[(carboxymethyl)thio]benzoic acid methyl ester (15.5 g). This intermediate was mixed with potassium bicarbonate solution (1 M, 160 mL) and then potassium permanganate solution (0.33 M in 0.42 M acetic acid, 750 mL) was slowly added at 20–30° C. (until the color of the permanganate was permanent). After 2 h stirring at 20–30° C., the residual permanganate was decolorized with saturated sodium pyrosulfite solution. The mixture was filtrated and the filtrate was acidified with hydrochloric acid (6 M) and the product was extracted with ethyl acetate. The extract was dried with sodium sulphate and evaporated to dryness (yield 3.5 g) $^1$H-NMR (400 MHz, DMSO-d$_6$) d=3.93 (s, 3H), 4.70 (s, 2H), 7.93 (d, J=11.1 Hz,1 H), 8.26 (dd, J=11.1 Hz, 2.8 Hz, 1H), 8.51 (d, J=2.8 Hz, 1H), 12.5 (b, 1H).

4-Chloro-3-(methylsulfonyl)benzoic acid methyl ester

4-Chloro-3-[(carboxymethyl)sulfonyl]benzoic acid methyl ester (5.6 g) was mixed with pyridine (10 mL) and the mixture was refluxed for 30 min and then cooled to room temperature. The product was precipitated by adding water (30 mL). The precipitate was filtered, washed with water and dried (yield 2.5 g). $^1$H-NMR (400 MHz, DMSO-d$_6$) d=3.43 (s, 3H), 3.92 (s, 3H), 7.92 (d, J=8.2 Hz, 1H), 8.24 (dd, J=8.2 Hz, 2.2 Hz, 1H), 8.53 (d, J=2.2 Hz, 1H).

4-Chloro-3-(methylsulfonyl)benzyl alcohol

To a suspension of 4-chloro-3-(methylsulfonyl)benzoic acid methyl ester (2.4 g) in tetrahydrofuran (50 mL) was added lithium triethylborohydride (1 M in tetrahydrofuran, 24 mL) at 0–5° C. under nitrogen. The mixture was stirred for 30 min and then more of lithium triethylborohydride (1M in tetrahydrofuran, 5 mL) was added and the mixture was further stirred for 60 min. Water (2 mL) was added and the tetrahydrofuran was evaporated under vacuum. Toluene (100 mL) and water (30 mL) were added and then hydrogen peroxide (30% in water, 20 mL) was added at 10–20° C. After 30 min the organic phase was separated and washed with potassium bicarbonate solution (1 M) and then dried with sodium sulphate and evaporated to dryness (yield 1.2 g). $^1$H-NMR (400 MHz, DMSO-d$_6$) d=3.36 (s, 3H), 4.59 (d, J=5.7 Hz, 2H), 5.52 (t, J=5.7 Hz, 1 H), 7.66 (dd, J=8.2 Hz, 2.1 Hz, 1H), 7.70 (d, J=8.2 Hz, 1H), 8.03 (d, J=2.1 Hz, 1H).

4-Chloro-3-(methylsulfonyl)benzaldehyde

4-Chloro-3-(methylsulfonyl)benzyl alcohol (1.0 g) was dissolved in dichloromethane (20 mL) and then active manganese(IV) oxide (4.2 g) was added and the mixture was stirred for 15 min at 22–28° C. The solid was removed by filtration and the filtrate was evaporated to dryness (yield 0.76 g). $^1$H-NMR (400 MHz, DMSO-d$_6$) d=3.44 (s, 3H), 8.00 (d, J=8.2 Hz, 1H), 8.23 (dd, J=8.2 Hz, 2.2 Hz, 1H), 8.53 (d, J=2.2 Hz, 1H), 10.12 (s, 1H).

3-{[4-Chloro-3-(methylsulfonyl)phenyl]methylene}-2,4-pentanedione

4-Chloro-3-(methylsulfonyl)benzaldehyde (760 mg), 2-propanol (10 mL), 2,4-pentanedione (0.8 mL), formic acid (22 mL) and piperidine (57 mL) were mixed and stirred at 22–25° C. for 20 h. The product was filtered, washed with 2-propanol and dried. The compound was purified by crystallization from toluene (15 mL, yield 790 mg, melting point 170–172° C.). $^1$H-NMR (400 MHz, DMSO-d$_6$) d=2.27 (s, 3H), 2.47 (s, 3H), 3.40 (s, 3H), 7.72 (dd, J=8.3 Hz, 2.2 Hz, 1H), 7.84 (d, J=8.3 Hz, 1H), 7.84 (s, 1H), 8.19 (d, J=2.2 Hz, 1H).

Example 6

3-{[3-Chloro-4(methylsulfonyl)-phenyl]methylene}-2,4-pentanedione

3-Chloro-4-methylsulfonylbenzaldehyde

To a solution containing 1.0 g of 4,3-dichlorobenzaldehyde in 45 ml of DMSO was added 1.93 g of methanesulfinicacid sodium salt with stirring at 90° C. The solution was stirred for 6 hours at 90° C. and then poured into water. Sodiumhydrogencarbonate was added and the product was extracted with ethyl acetate. The extract was evaporated to dryness in vacuo. The residue was triturated with 2-propanol, yield 1.06 g. $^1$H-NMR (DMSO-d$_6$, 400 MHz): 3.45 (s, 3 H, CH$_3$), 8.09–8.27 (m, 3 H, Ar), 10.01 (d, 1 H, CHO).

3-{[3-Chloro-4-(methylsulfonyl)-phenyl]methylene}-2,4-pentanedione

To a solution containing 2.5 g of 3-chloro-4-methylsulfonylbenzaldehyde, 0.13 ml of piperidine and 0.05 ml of formic acid in 70 ml of 2-propanol was added 2.6 ml of 2,4-pentanedione with stirring at 20° C. The solution was stirred overnight at 20° C. The product was filtrated and washed with 2-propanol, yield 2.1 g (60%), mp. 140–142°

C. $^1$H-NMR (DMSO-d$_6$,400 MHz): 2.28 (s, 3 H, CH$_3$), 2.50 (s, 3 H, CH$_3$), 3.40 (s, 3 H, CH$_3$), 7.60 (m, 1 H, Ar), 7.80 (m, 1 H, Ar), 7.77 (s, 1 H CH), 8.1 (m, 1 H, Ar).

Example 7

Platelet Activation Factor (PAF) Induced Airway Eosinophilia

The effect of the compounds of the invention was evaluated using platelet activating factor (PAF) induced airway eosinophilia model. Budesonide, a widely used inhaled corticosteroid in the treatment of human asthma, was tested as a reference compound.

PAF induced eosinophil accumulation into the guinea-pig lung is a widely used animal model for human asthma. Inflammation of the airways is a characteristic feature of bronchial asthma and is associated with eosinophil and lymphocyte accumulation in the airway wall and lumen. In guinea-pigs, eosinophilia can be induced by local administration of platelet activating factor into the airways. IL-5, an eosinophil growth factor and activator, is one important mediator of the PAF-induced eosinophilia (Whelan, C. J., Inflamm. Res. 45:166–170 (1996)). Glucocorticoids inhibit PAF eosinophilia in guinea-pigs and the effect is thought to come through inhibition of IL-5 production.

The test was carried out by infusing the compound to be tested into the airways at the rate of 100 μl/min for 5 minutes. One hour later the guinea-pigs were exposed to 2.5 μg PAF intratracheally within 5 minutes by an infusion at a rate of 100 μl/min. 24 h after PAF, the lungs were lavaged with saline and the number of eosinophils in the broncho-alveolar lavage fluid (BALF) was counted.

Figure 2:
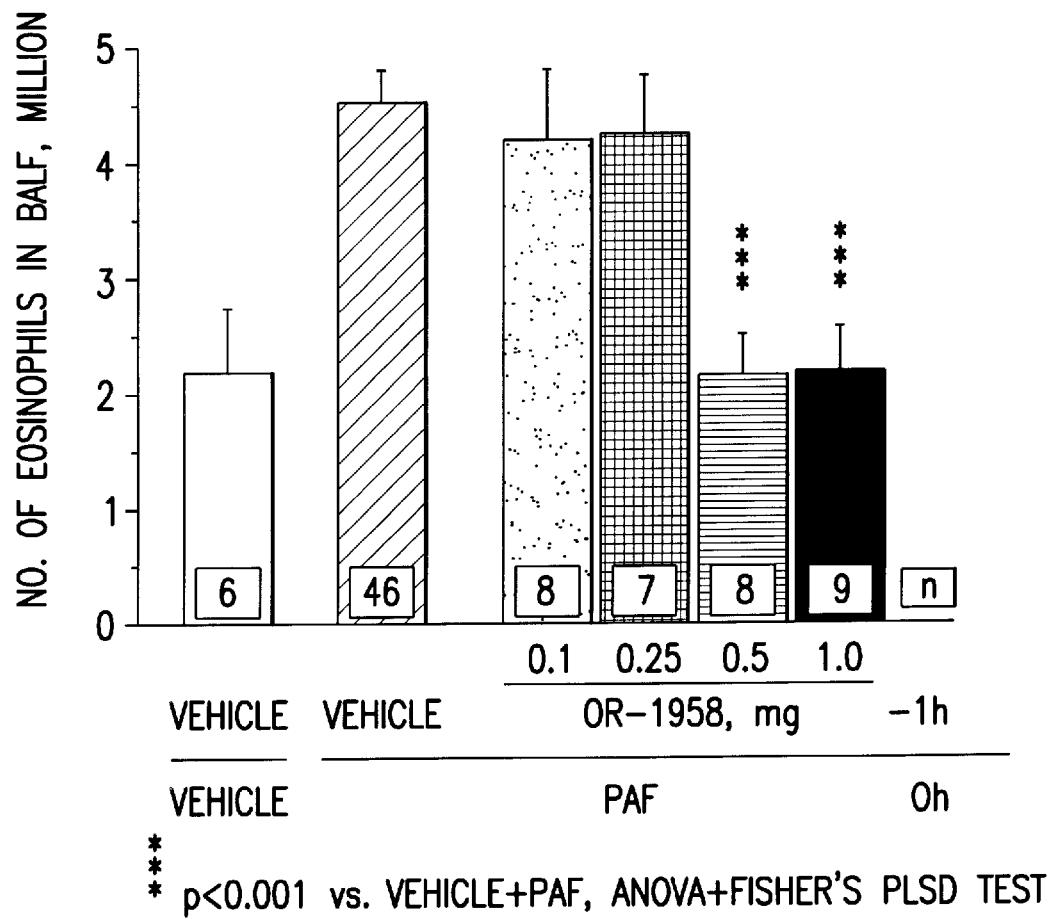
FIG. 2 shows the effect of 3-[(3-chloro-4-methylsulfonylphenyl)methylene]-2,4-pentanedione (test compound OR 1958) on PAF-induced eosinophil accumulation.

FIG. 1 shows the effect of 3-[(4-methylsulfonylphenyl) methylene]-2,4-pentanedione (test compound OR 1384) and the reference compound, budesonide on PAF-induced eosinophil accumulation. FIG. 2 shows the corresponding results with 3-[(3-chloro-4-methylsulfonylphenyl)methylene]-2,4-pentanedione (test compound OR 1958). According to these results the compounds of the invention decreases the eosinophil accumulation to the level of the vehicle in a dose dependent manner indicating the total inhibition of the airway eosinophilia.

Local Irritative Effect

Several studies were performed to compare the local irritative effect of the compounds of the invention (3-[(3-chloro-4-methylsulfonylphenyl)-methylene]-2,4-pentanedione and 3-[(4-methylsulfonylphenyl)methylene]-2,4-pentanedione) and OR-1364. The compounds of the invention could be given as an aerosol or intratracheally as a powder to a guinea pig at doses up to 3 mg/kg without any signs of irritation. On the contrary, when OR 1364 was given as an aerosol (1 mg/ml/15 min), there was a significant decrease in respiratory rate indicating sensory irritation by this compound.

Furthermore, in rabbits, the vein irritation was studied by giving 8 mg of the compounds intravenously to the marginal ear vein. The compounds of the invention had no irritative effect while OR 1364 induced clear irritation.

In accordance, OR 1364 in the form of a 20% creme (w/w) was prepared by dissolving 2.00 g of the active ingredient in 2 ml of absolute ethanol and then mixing it to add 10 g of the commercially available lotion Humektan™. OR 1364 in the form of a 20% creme (w/w) induced both macroscopic and histological irritation of the rabbit skin, while the compound of the invention had no effect.

Therefore it can be concluded, that the compounds of the invention do not induce local irritation, while the irritative effect is an obstacle for the local use of OR 1364 in the airways.

Dry Powder Inhalation Formulation

| Ingredient | Amount per 1 kg |
|---|---|
| Active ingredient* | 26.25 g |
| Lactose (450 mesh) | 194.75 g |
| Lactose (325 mesh) | 779.00 g |

*3-[(3-chloro-4-methylsulfonylphenyl)methylene]-2,4-pentanedione

Micronised active ingredient is mixed with an inert carrier, lactose in three steps. Lactose (450 mesh) and a part of lactose (325 mesh) and the active ingredient are added into the blender and mixed until the powder mixture is homogenous. The mixture of lactose grades and the active ingredient is sieved. The screening of the powder mixture reduces the number of particle clusters present. Thereafter, part of lactose (325 mesh) is added into the blender and mixed further. Thirdly, the rest of the lactose (325 mesh) is added and mixed until the powder is again homogenous. The manufactured inhalation powder mixture is packed into a multiple dose powder inhaler device.

What is claimed is:

1. Compounds of general formula I:

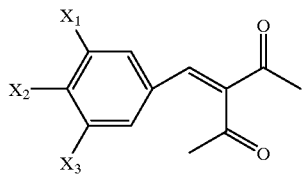

wherein one of X$_1$ and X$_2$ is MeSO$_2$ and the other one is halogen and X$_3$ is hydrogen or halogen.

2. The compound of formula I wherein X$_1$ is halogen, X$_2$ is MeSO$_2$ and X$_3$ is hydrogen.

3. 3-{[3-Fluoro-4-(methylsulfonyl)-phenyl]methylene}-2,4-pentanedione.

4. 3-{[3-Chloro-4-(methylsulfonyl)-phenyl]methylene}-2,4-pentanedione.

5. 3-{[3-Bromo-4-(methylsulfonyl)-phenyl]methylene}-2,4-pentanedione.

6. 3-{[3,5-Dichloro-4-(methylsulfonyl)phenyl]methylene}-2,4-pentanedione.

7. 3-{[4-Chloro-3-(methylsulfonyl)phenyl]methylene}-2,4-pentanedione.

8. An inhalable pharmaceutical formulation containing a compound of formula I:

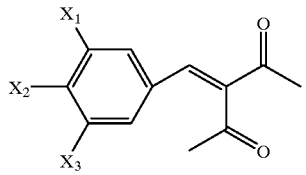

wherein one of X$_1$ and X$_2$ is MeSO$_2$ and the other one is halogen and X$_3$ is hydrogen or halogen, having about 100% of its particle size below 10 μm, optionally in a suitable carrier or diluent.

9. The formulation according to claim 8, wherein the carrier is lactose.

10. The formulation according to claim 8, wherein it is a dry inhalation formulation.

11. A method for the prevention or treatment of inflammatory respiratory diseases wherein said method comprises administering to a mammal in need of said prevention or treatment an effective amount of the compound of general formula I':

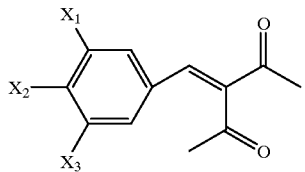

wherein one of $X_1$ and $X_2$ is $MeSO_2$ and the other one is hydrogen or halogen and $X_3$ is hydrogen or halogen to prevent or treat said inflammatory respiratory diseases.

12. The method of claim 11, wherein the compound is 3-[(4-methylsulfonylphenyl)methylene]-2,4-pentanedione.

13. The method of claim 11, wherein the compound is 3-[(3-chloro-4-methylsulfonylphenyl)methylene]-2,4-pentanedione.

14. The method of claim 11, wherein the disease is asthma.

15. The method of claim 11, wherein the disease is steroid-resistant asthma.

16. The method of claim 11, wherein the disease is Acute Respiratory Distress Syndrome.

17. The method of claim 11, wherein the disease is chronic obstructive pulmonary disease.

* * * * *